United States Patent
Yang et al.

(10) Patent No.: US 9,663,425 B2
(45) Date of Patent: May 30, 2017

(54) METHOD TO PRODUCE 1,1,2,3-TETRACHLOROPROPENE WITH HIGH YIELD

(71) Applicant: Honeywell International Inc., Morristown, NJ (US)

(72) Inventors: Terris Yang, East Amherst, NY (US); Hsueh Sung Tung, Getzville, NY (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 14/658,460

(22) Filed: Mar. 16, 2015

(65) Prior Publication Data

US 2015/0274616 A1  Oct. 1, 2015

Related U.S. Application Data

(60) Provisional application No. 61/972,673, filed on Mar. 31, 2014.

(51) Int. Cl.
*C07C 17/25* (2006.01)
*C07C 17/087* (2006.01)
*C07C 17/04* (2006.01)

(52) U.S. Cl.
CPC ............. *C07C 17/25* (2013.01); *C07C 17/04* (2013.01); *C07C 17/087* (2013.01)

(58) Field of Classification Search
CPC ..................................................... C07C 17/25
See application file for complete search history.

(56) References Cited

U.S. PATENT DOCUMENTS

| | | | |
|---|---|---|---|
| 3,926,758 A | 12/1975 | Smith | |
| 4,535,194 A * | 8/1985 | Woodard | C07C 17/04 570/220 |
| 4,650,914 A | 3/1987 | Woodard | |
| 8,058,486 B2 | 11/2011 | Merkel et al. | |
| 8,115,038 B2 * | 2/2012 | Wilson | C07C 17/10 570/227 |
| 8,258,355 B2 | 9/2012 | Merkel et al. | |
| 2012/0065434 A1 * | 3/2012 | Nose | C07C 17/206 570/160 |
| 2012/0078020 A1 * | 3/2012 | Elsheikh | C07C 17/206 570/160 |
| 2012/0289751 A1 | 11/2012 | Nose | |
| 2014/0221705 A1 * | 8/2014 | Wang | C07C 17/358 570/220 |

FOREIGN PATENT DOCUMENTS

| | | |
|---|---|---|
| CN | 101955414 A | 1/2011 |
| WO | 2013022677 A1 | 2/2013 |

* cited by examiner

*Primary Examiner* — Jafar Parsa
*Assistant Examiner* — Medhanit Bahta
(74) *Attorney, Agent, or Firm* — Bruce O. Bradford

(57) ABSTRACT

The present invention provides a method for the high yield production of HCC-1230xa from the known four step method, wherein the Step 3 crude product (crude HCC-240db) is used directly as the starting material in the Step 4 reaction—but only if the crude HCC-240db contains less than 0.5 wt % of impurities selected from the group consisting of HCC-250fb, HCC-1240za, and mixtures thereof.

14 Claims, No Drawings

METHOD TO PRODUCE 1,1,2,3-TETRACHLOROPROPENE WITH HIGH YIELD

CROSS-REFERENCE TO RELATED APPLICATION

This application claims domestic priority from commonly owned, U.S. Provisional Patent Application Ser. No. 61/972,673, filed 31 Mar. 2014, the disclosure of which is hereby incorporated herein by reference.

BACKGROUND OF THE INVENTION

As disclosed in U.S. Pat. No. 8,058,486, the compound 1,1,2,3-tetrachloro-propene (HCC-1230xa) is an important precursor that can be used for the production of 2,3,3,3-tetrafluoropropene (HFO-1234yf), which is a low GWP molecule that can be used as an effective refrigerant, fire extinguishing agent, heat transfer medium, propellant, foaming agent, blowing agent, gaseous dielectric agent, sterilant carrier, polymerization medium, particulate removal fluid, carrier fluid, buffing abrasive agent, displacement drying agent and power cycle working fluid, to name but a few.

HCC-1230xa can be made in a known four-step process, as follows:

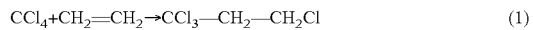  (1)

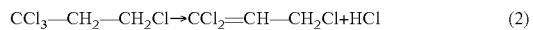  (2)

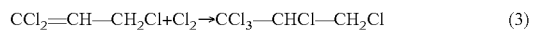  (3)

and

  (4)

As shown above, in Step 3 of this four-step process, 1,1,3-trichloropropene (HCC-1240za) from Step 2 is used as the starting material, where HCC-1240za is chlorinated by $Cl_2$ to form the intermediate product 1,1,1,2,3-pentachloropropane (HCC-240db) under specific reaction conditions:

Then, HCC-240db is dehydrochlorinated by a catalyst (such as $FeCl_3$ or equivalents) to form HCC-1230xa and HCl in Step 4:

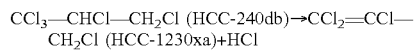

In normal practice, the crude product from the third step is used directly as the starting material for the fourth step reaction without further purification.

In this invention, it has been found that the crude HCC-240db containing HCC-1240za from the Step 3 reaction and/or HCC-250fb (1,1,1,3-tetrachloropropane) carried over from the Step 2 distillation, inhibited the conversion of HCC-240db to HCC-1230xa in the Step 4 reaction.

SUMMARY OF THE INVENTION

The present invention is based on the discovery that, when using HCC-240db containing different concentrations of HCC-1240za and HCC-250fb as the starting material to make HCC-1230xa, the amounts of HCC-1240za and HCC-250fb in the starting material have significant impact on HCC-240db conversion in the Step 4 reaction of HCC-240db to HCC-1230xa.

Thus, one embodiment of the present invention is a process for the dehydrochlorination of HCC-240db to produce HCC-1230xa in high yield comprising the steps of:

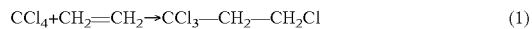  (1)

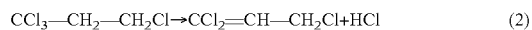  (2)

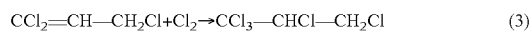  (3)

and

  (4)

wherein the crude HCC-240db in the Step (4) reaction contains less than 0.5 wt % of impurities selected from the group consisting of HCC-250fb, HCC-1240za, and mixtures thereof. The terms high yield, as used herein, mean at least 85% yield, preferably at least 90% percent yield, more preferably at least 95% yield, and most preferably at least 98% yield.

In certain embodiments, the reaction takes place in a liquid phase reactor in the presence of caustic solution or a dehydrochlorination catalyst.

In certain embodiments, the dehydrochlorination catalyst comprises one or more metal halides such as $FeCl_3$, $AlCl_3$, and the like.

In certain embodiments, the crude HCC-240db from Step 3 reaction is used directly as the starting material.

In certain embodiments, the combined HCC-1240za and HCC-250fb concentration in the crude HCC-240db starting material is less than 0.5 wt % to gain high yield on HCC-1230xa.

In certain embodiments, crude HCC-240db containing over 0.5 wt % of HCC-1240za/HCC-250fb must first be purified to remove impurities selected from the group consisting of HCC-250fb, HCC-1240za, and mixtures thereof.

In certain embodiments, vacuum distillation or another purification method is used to remove the impurities HCC-1240za and/or HCC-250fb from the crude HCC-240db. Examples of other purification methods include distillations under elevated or atmospheric pressure, adsorption with activated carbon/molecular sieves/resins, and the like.

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

DETAILED DESCRIPTION OF THE INVENTION

As described above, in order to obtain a high yield of HCC-1230xa from the known four step reactions, the Step 3 crude product (crude HCC-240db) is used directly as the starting material in Step 4 reaction if the crude HCC-240db contains less than 0.5 wt % of impurities selected from the group consisting of HCC-250fb, HCC-1240za, and mixtures thereof. However, a purification process (such as vacuum distillation) is implemented to remove the HCC-1240za and/or HCC-250fb impurities from the crude HCC-240db, if it contains more than 0.5 wt % of HCC-1240za and/or HCC-250fb prior to the Step (4) reaction, if high yields of HCC-1230xa are to be achieved.

In one example, at 120° C., with 1.0 wt % of $FeCl_3$ and 2 hours of residence time, only 14.7 mol % of HCC-240db conversion was observed. With the residence time extended to 6 hours, the HCC-240db conversion was improved marginally to 16.6 mol %. Both examples used a crude HCC-240db containing 2.0 wt % of 1240za, 2.3 wt % 250fb and 92.5 wt % 240db. Increasing reaction temperature to 140° C. and $FeCl_3$ concentration to 2.0 wt % improved HCC-240db conversion (54.9 mol %), but still at very low level.

With HCC-1240za and HCC-250fb being removed from the above starting material by vacuum distillation, at 120° C., with 1.0 wt % of $FeCl_3$ and 2 hours of residence time, HCC-240db conversion was significantly increased to 99.3 mol %.

It was thus concluded that the existence of impurities selected from the group consisting of HCC-250fb, HCC-1240za, and mixtures thereof in Step 3 crude product inhibits the dehydrochlorination of HCC-240db, causing a low yield to HCC-1230xa.

Due to the fact that HCC-250fb is dehydrochlorinated by $FeCl_3$ to form HCC-1240za during Step 4 reaction, and HCC-1240za is further dimerized in the process, it is also possible that the products of HCC-1240za dimerization (pentachlorocyclohexene and/or hexachlorocyclohexane isomers) have the similar impact on HCC-240db conversion.

In order to gain high HCC-1230xa yield (or high HCC-240db conversion) in the dehydrochlorination of HCC-240db to produce HCC-1230xa, the starting material of the Step 3 reaction is HCC-250fb free (<0.5 wt %). On the other hand, the Step 3 reaction is controlled to have HCC-1240za fully converted with HCC-1240za concentration in the crude product less than 0.5 wt % in order to use the Step 3 crude product directly in Step 4 without purification.

If the total concentration of the impurities selected from the group consisting of HCC-250fb, HCC-1240za, and mixtures thereof in the Step 3 crude product is higher than 0.5 wt %, the crude product is purified to remove the HCC-1240za and HCC-250fb impurities using known separation methods such as vacuum distillation and the like.

EXAMPLES

The following examples are provided to further illustrate the invention and should not be taken as limitations of the invention.

Example 1

A 500 ml glass flask (reactor) equipped with a magnetic stirring bar and a total condenser was charged with 298.5 g HCC-240db (Containing 99.3 wt % of HCC-240db, balanced with HCC-1230xa) and 1.49 g anhydrous $FeCl_3$. The reactor was stirred and heated to 120±2° C. via an oil bath. After two hours, the reactor was removed from the oil bath and cooled down to room temperature. Then the mixture in the reactor was filtered, washed with deionized (D.I.) water and dried with $MgSO_4$. By GC analysis, the reaction mixture contained 99.6 wt % of HCC-1230xa and 0.15 wt % of HCC-240db, representing a HCC-240db conversion of 99.9 mol % and HCC-1230xa selectivity of 99.7 mol %.

Example 2

300.0 g HCC-240db (containing 92.1 wt % of HCC-240db, 0.1 wt % of HCC-1230xa, 3.0 wt % of HCC-250fb, balanced with others) and 3.0 g anhydrous $FeCl_3$ were charged into the reactor with the same reaction conditions and procedure followed as described in Example 1. By GC analysis, the reaction mixture contained 0.3 wt % of HCC-1240za, 0 wt % of HCC-250fb, 45.4 wt % of HCC-1230xa and 48.6 wt % of HCC-240db, representing a HCC-240db conversion of 51.5 mol % and HCC-1230xa selectivity of 100 mol %.

Example 3

296.7 g HCC-240db (containing 88.1 wt % of HCC-240db, 0.1 wt % of HCC-1230xa, 7.2 wt % of HCC-1240za, 0.1 wt % of HCC-250fb, balanced with others) and 2.97 g anhydrous $FeCl_3$ were charged into the reactor with the same reaction conditions and procedure followed as described in Example 1. By GC analysis, the reaction mixture contained 1.6 wt % of HCC-1240za, 0 wt % of HCC-250fb, 22.2 wt % of HCC-1230xa and 69.5 wt % of HCC-240db, representing a HCC-240db conversion of 22.1 mol % and HCC-1230xa selectivity of 100 mol %.

Example 4

298.7 g HCC-240db (containing 87.0 wt % of HCC-240db, 0.6 wt % of HCC-1230xa, 1.9 wt % of HCC-1240za, 8.0 wt % of HCC-250fb, balanced with others) and 2.99 g anhydrous $FeCl_3$ were charged into the reactor with the same reaction conditions and procedure followed as described in Example 1. By GC analysis, the reaction mixture contained 2.5 wt % of HCC-1240za, 0 wt % of HCC-250fb, 12.3 wt % of HCC-1230xa and 79.0 wt % of HCC-240db, representing a HCC-240db conversion of 9.3 mol % and HCC-1230xa selectivity of 100 mol %.

Example 5

300.2 g HCC-240db (containing 92.5 wt % of HCC-240db, 2.0 wt % of HCC-1240za, 2.3 wt % of HCC-250fb, 0.6 wt % of HCC-1230xa, balanced with others) and 6.0 g anhydrous $FeCl_3$ were charged into the reactor with the same reaction conditions and procedure followed as described in Example 1, except for the reaction temperature increased to 140° C. By GC analysis, the reaction mixture contained 0.5 wt % of HCC-1240za, 0 wt % of HCC-250fb, 49.5 wt % of HCC-1230xa and 44.9 wt % of HCC-240db, representing a HCC-240db conversion of 54.9 mol % and HCC-1230xa selectivity of 100 mol %.

Example 6

A 250 ml glass flask (reactor) equipped with a magnetic stirring bar and a total condenser was charged with 100 g HCC-240db (containing 98.8 wt % of HCC-240db, 1.0 wt % of HCC-1240za, balanced with HCC-1230xa) and 1.0 g anhydrous $FeCl_3$. The reactor was stirred and heated to 120±2° C. via an oil bath. After 2 hours, the reactor was removed from the oil bath and cooled down to room temperature. Then the mixture in the reactor was filtered, washed with deionized (D.I.) water and dried with $MgSO_4$. By GC analysis, the reaction mixture contained 81.7 wt % of HCC-1230xa, 0.03 wt % of HCC-1240za and 18.2 wt % of HCC-240db, representing a HCC-240db conversion of 84.2 mol % and HCC-1230xa selectivity of 100 mol %.

Example 7

100 g HCC-240db (containing 99.3 wt % of HCC-240db, 0.6 wt % of HCC-1240za, balanced with HCC-1230xa) and 1.0 g anhydrous FeCl$_3$ were charged into the reactor with the same reaction conditions and procedure followed as described in Example 6. By GC analysis, the reaction mixture contained 0 wt % of HCC-1240za, 99.4 wt % of HCC-1230xa and 0.2 wt % of HCC-240db, representing a HCC-240db conversion of 99.8 mol % and HCC-1230xa selectivity of 100 mol %.

Example 8

100 g HCC-240db (containing 99.6 wt % of HCC-240db, 0.25 wt % of HCC-1240za, balanced with HCC-1230xa) and 1.0 g anhydrous FeCl$_3$ were charged into the reactor with the same reaction conditions and procedure followed as described in Example 6. By GC analysis, the reaction mixture contained 0 wt % of HCC-1240za, 99.6 wt % of HCC-1230xa and 0.1 wt % of HCC-240db, representing a HCC-240db conversion of 99.9 mol % and HCC-1230xa selectivity of 100 mol %.

Example 9

A 5 Gallon glass-lined reactor equipped with an agitator and a total condenser was charged with 45 lb HCC-240db (containing 92.5 wt % of HCC-240db, 2.0 wt % of HCC-1240za, 2.3 wt % of HCC-250fb, 0.6 wt % of HCC-1230xa, balanced with others) and 204.5 g anhydrous FeCl$_3$. The reactor was stirred and heated to 120±2° C. by 30# steam. After two hours, the reactor was cooled down to room temperature. Then the crude product was filtered and a sample of the crude product was washed with deionized (D.I.) water and dried with MgSO$_4$. By GC analysis, the filtered crude product contained 0.97 wt % of HCC-1240za, 0.1 wt % of HCC-250fb, 13.9 wt % of HCC-1230xa and 79.6 wt % of HCC-240db, representing a HCC-240db conversion of 14.7 mol % and HCC-1230xa selectivity of 100 mol %.

Example 10

45 lb HCC-240db (containing 92.5 wt % of HCC-240db, 2.0 wt % of HCC-1240za, 2.3 wt % of HCC-250fb, 0.6 wt % of HCC-1230xa, balanced with others) and 204.5 g anhydrous FeCl$_3$ were charged into the reactor with the same reaction conditions and procedure followed as described in Example 6, except for the reaction time increased from 2 hours to 6 hours. By GC analysis, the filtered crude product contained 0.95 wt % of HCC-1240za, 0.1 wt % of HCC-250fb, 15.7 wt % of HCC-1230xa and 78.3 wt % of HCC-240db, representing a HCC-240db conversion of 16.6 mol % and HCC-1230xa selectivity of 100 mol %.

Example 11

60 lb HCC-240db (containing 95.6 wt % of HCC-240db, 0 wt % of HCC-1240za, 0 wt % of HCC-250fb, 0.3 wt % of HCC-1230xa, balanced with others) and 272 g anhydrous FeCl$_3$ were charged into the reactor with the same reaction conditions and procedure followed as described in Example 6. By GC analysis, the filtered crude product contained 94.1 wt % of HCC-1230xa and 0.8 wt % of HCC-240db, representing a HCC-240db conversion of 99.3 mol % and HCC-1230xa selectivity of 99.7 mol %.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for the dehydrochlorination of crude 1,1,1,2,3-pentachloropropane (HCC-240db) to produce 1,1,2,3-tetrachloro-1-propene (HCC-1230xa) with at least 85% yield including the following step (4):

$$CCl_3-CHCl-CH_2Cl \rightarrow CCl_2=CCl-CH_2Cl+HCl \quad (4)$$

wherein the crude CCl$_3$—CHCl—CH$_2$Cl (HCC-240db) contains one or more impurities selected from the group consisting of 1,1,1,3-tetrachloropropane (HCC-250fb), 1,1,3-trichloropropene (HCC-1240za), and mixtures thereof; and wherein the reaction takes place in a liquid phase reactor in the presence of a caustic solution.

2. The process of claim 1, wherein the process further includes Step (3) which precedes Step (4):

$$CCl_2=CH-CH_2Cl+Cl_2 \rightarrow CCl_3-CHCl-CH_2Cl \quad (3)$$

and wherein the crude HCC-240db from Step 3 reaction is used directly as the starting material in Step (4).

3. The process of claim 2, wherein HCC-250fb concentration in the crude HCC-240db starting material is up to 0.5 wt %.

4. The process of claim 2, wherein HCC-1240za concentration in the crude HCC-240db starting material is up to 0.5 wt %.

5. The process of claim 2, wherein the combined HCC-1240za and HCC-250fb concentration in the crude HCC-240db starting material is up to 0.5 wt %.

6. The process of claim 1, further comprising purifying crude HCC-240db containing impurities comprising over 0.5 wt % of HCC-1240za, HCC-250fb, or a mixture thereof, to remove the impurities to a level below 0.5 wt %.

7. The process of claim 6, wherein vacuum distillation or other purification method is used to remove the impurities from the crude HCC-240db.

8. A process for the dehydrochlorination of crude 1,1,1,2,3-pentachloropropane (HCC-240db) to produce 1,1,2,3-tetrachloro-1-propene (HCC-1230xa) comprising the reaction steps of:

$$CCl_4+CH_2=CH_2 \rightarrow CCl_3-CH_2-CH_2Cl \quad (1)$$

$$CCl_3-CH_2-CH_2Cl \rightarrow CCl_2=CH-CH_2Cl+HCl \quad (2)$$

$$CCl_2=CH\text{-}CH_2Cl+Cl_2 \rightarrow CCl_3\text{—}CHCl\text{—}CH_2Cl \quad (3)$$

and $$CCl_3\text{—}CHCl\text{—}CH_2Cl \rightarrow CCl_2=CCl\text{-}CH_2Cl+HCl \quad (4)$$

wherein the crude CCl$_3$—CHCl—CH$_2$Cl (HCC-240db) contains one or more impurities selected from the group consisting of 1,1,1,3-tetrachloropropane (HCC-250fb), 1,1,3-trichloropropene (HCC-1240za), and mixtures thereof, and wherein the impurities are present at up to 0.5 wt %: and
  wherein the reaction takes place in a liquid phase reactor in the presence of a caustic solution.

9. The process of claim 8, wherein the crude HCC-240db from Step 3 reaction is used directly as the starting material.

10. The process of claim 9, wherein the HCC-250fb concentration in the crude HCC-240db starting material is up to 0.5 wt %.

11. The process of claim 9, wherein HCC-1240za concentration in the crude HCC-240db starting material is up to 0.5 wt %.

12. The process of claim 9, wherein the combined HCC-1240za and HCC-250fb concentration in the crude HCC-240db starting material is up to 0.5 wt %.

13. The process of claim 8, further comprising purifying a crude HCC-240db containing impurities comprising over 0.5 wt % selected from HCC-1240za, HCC-250fb, or a mixture thereof, to reduce the impurities to a level that is up to 0.5 wt %.

14. The process of claim 13, wherein vacuum distillation or other purification method is used to remove the impurities from the crude HCC-240db.

\* \* \* \* \*